(12) United States Patent
Matsuoka

(10) Patent No.: US 6,207,136 B1
(45) Date of Patent: *Mar. 27, 2001

(54) FLUORESCENT IMAGING METHOD OF SACCHARIDE UPTAKE ACTIVITY OF LIVING TISSUE

(75) Inventor: Hideaki Matsuoka, Musashino (JP)

(73) Assignee: Tokyo University of Agriculture and Technology, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/007,410

(22) Filed: Jan. 15, 1998

(30) Foreign Application Priority Data

Mar. 11, 1997 (JP) ..................................................... 9-072801

(51) Int. Cl.⁷ .............................. A61B 10/00; A61B 5/00; A61B 8/00
(52) U.S. Cl. ............................ 424/9.6; 424/1.73; 424/9.3
(58) Field of Search ................................... 424/1.11, 1.65, 424/1.73, 9.1, 9.6, 9.7, 9.8, 9.81; 127/30, 36; 514/23; 436/95; 536/1.11; 422/82.08; 252/301.16; 250/458.1; 206/569, 570

(56) References Cited

PUBLICATIONS

Biochimica et Biophysica Acta 1289 (1996) 5–9, by K. Yoshioka et al.

Biosci. Biotech. Biochem., 60 (11), 1899–1901, 1996, by K. Yoshioka et al.

Appl. Microbiol. Biotechnol. (1996) 46:400–404, by K. Yoshioka et al.

Journal of Neurochemistry, 1977, vol. 28, pp. 897–916, by L. Sokoloff et al.

Biochimica et Biophysica Acta 815 (1985) 75–84, by L. Speizer et al.

Histochemical Journal 26, 207–212 (1994), by M. Shimada et al.

Dox et al, *The Harper Collins Illustrated Medical Dictionary*, pp. 187 and 425, 1993.*

Satoh et al, Hum. Cell, vol. 11. No. 4, pp. 191–198, Application of Real Time Confocal Microscopy for Observation of Living Cells, in Tissue Specimens, Dec. 1998.*

* cited by examiner

Primary Examiner—Dameron Jones
(74) Attorney, Agent, or Firm—Flynn, Thiel, Boutell & Tanis, P.C.

(57) ABSTRACT

A fluorescent imaging method of the changes in viability of living bodies wherein the living bodies are provided with a chemical or physical exterior stimulation and information on the changes in viability of cells caused by the stimulation is obtained by means of a fluorescent imaging method of the saccharide uptake activity by contacting or administering to the living bodies an aqueous solution of a fluorescent saccharide compound which includes at its specific position a saccharide molecule chemically combined with a fluorescent pigment molecule.

7 Claims, 5 Drawing Sheets

Fig_1
PREPARATION OF FLUORESCENT GLUCOSE REAGENT
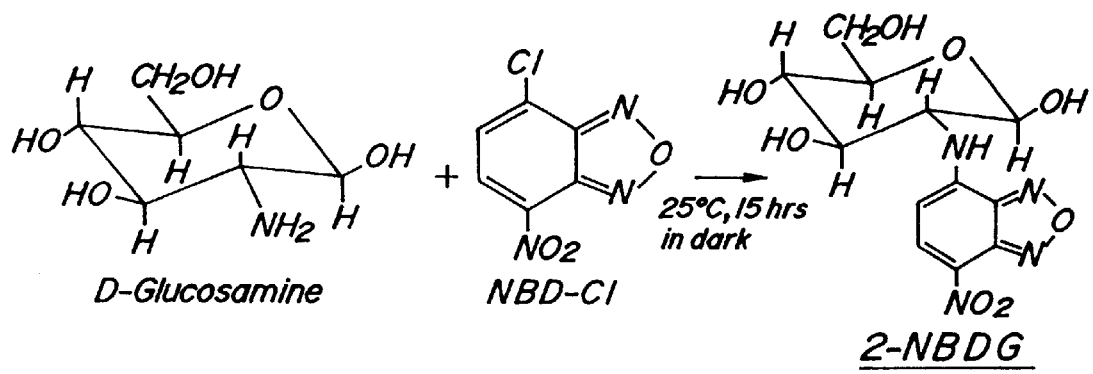
NBD-Cl: N-(7-nitrobenz-2-oxa-1,3-diazol-4yl-)amino chloride
2-NBDG: 2-(N-(7-nitrobenz-2-oxa-1,3-diazol-4-yl)amino)
-2-deoxy-D-glucose

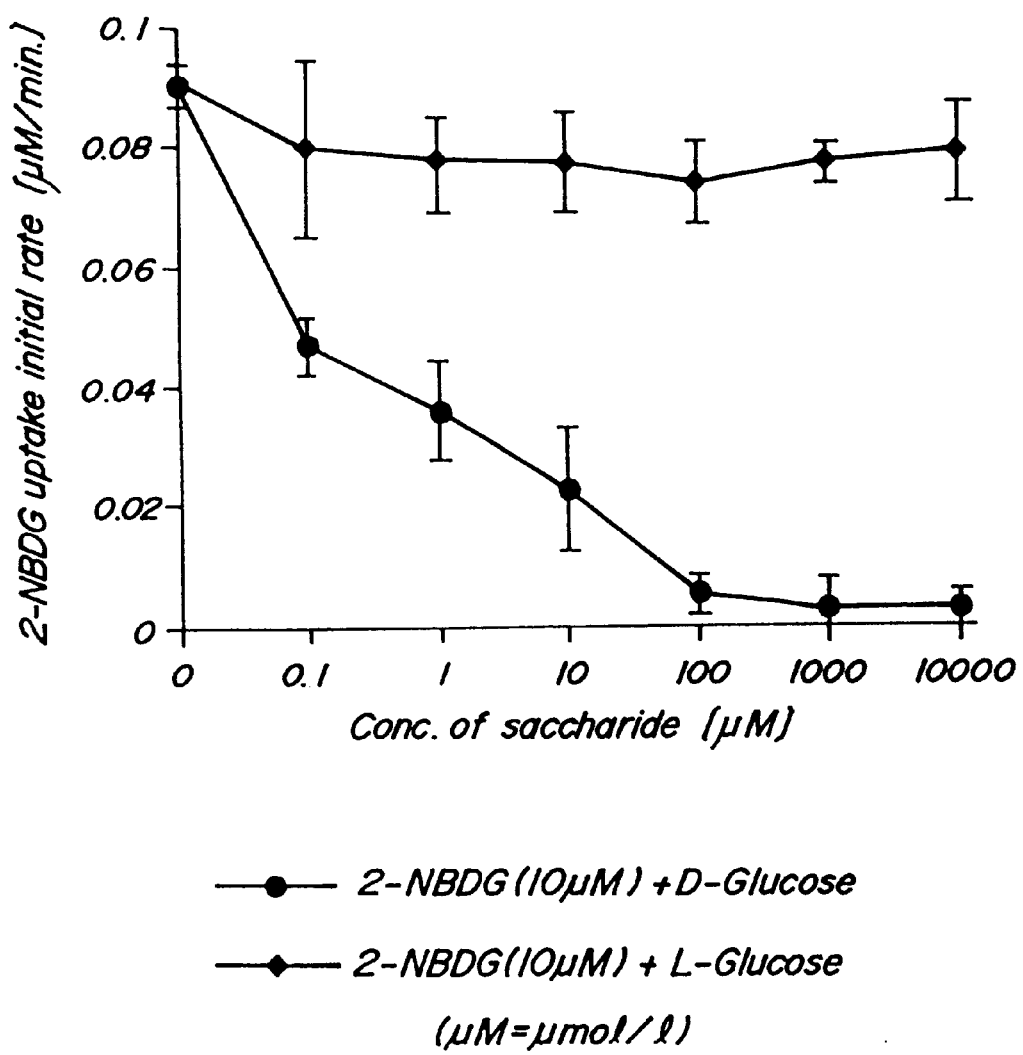

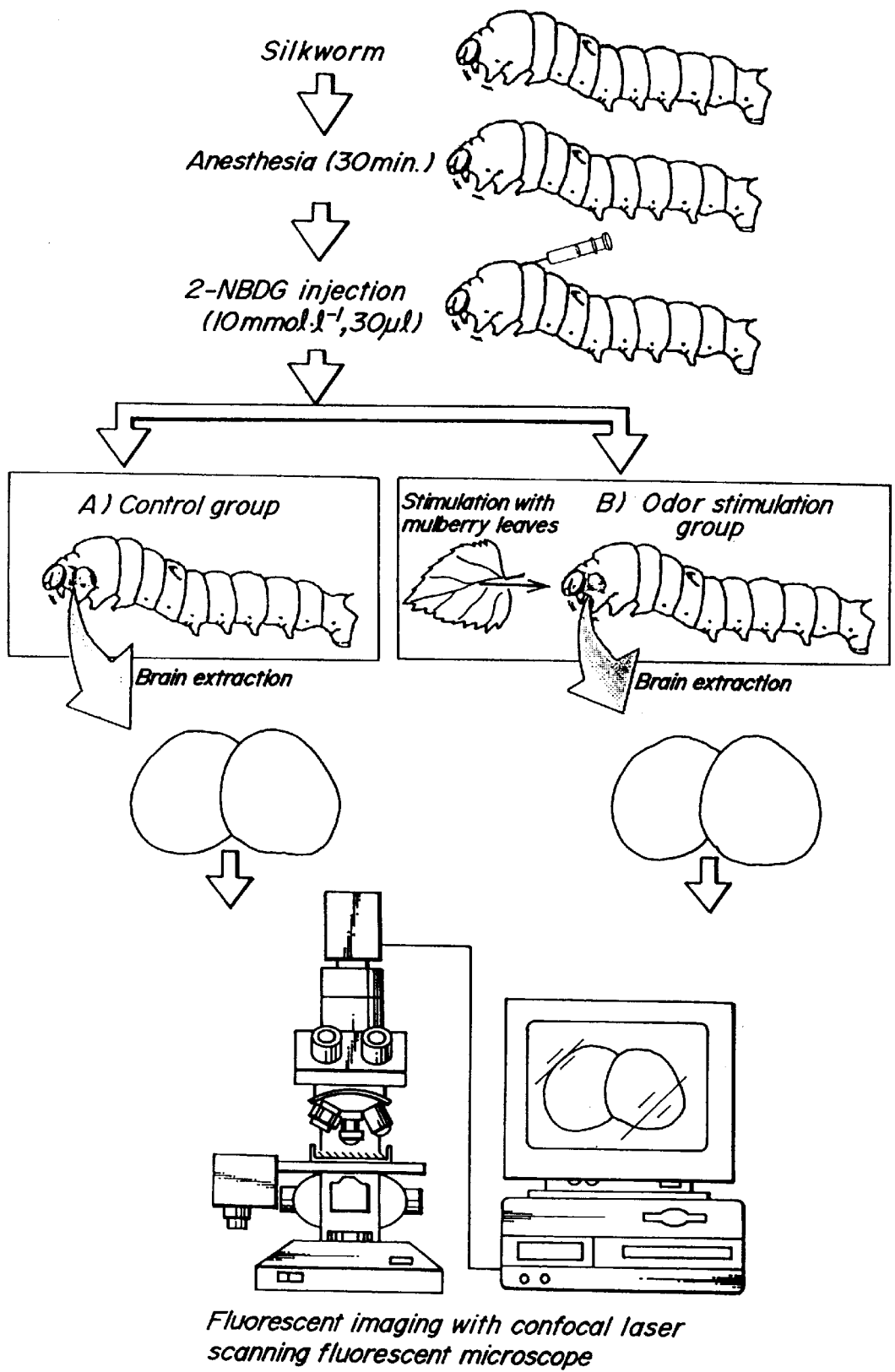
Fig. 3 ADMINISTRATION OF 2-NBDG AND ODOR STIMULATION OF SILKWORM AND OBSERVATION OF BRAINS

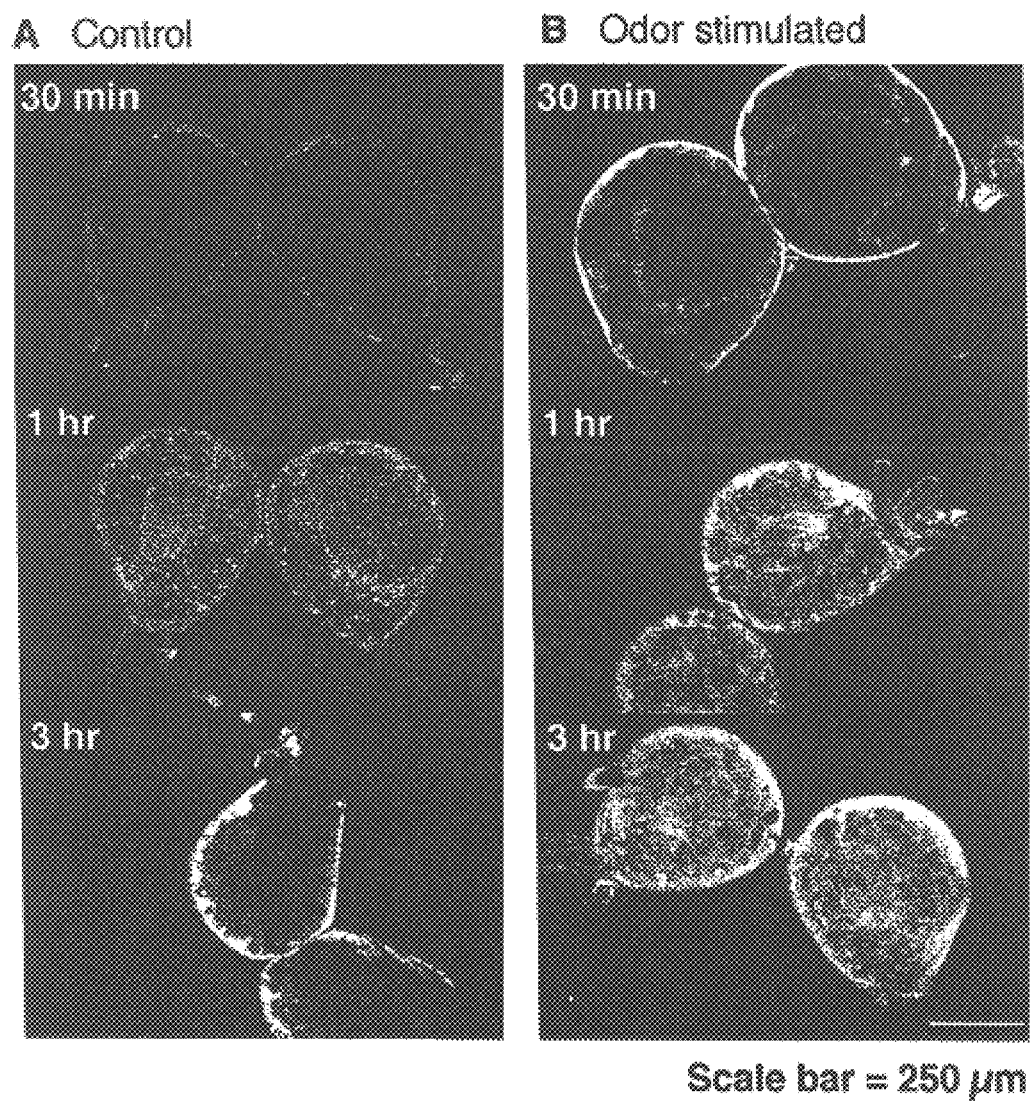
Fig. 4 Imaging of 2-NBDG uptake in the silkworm brain.

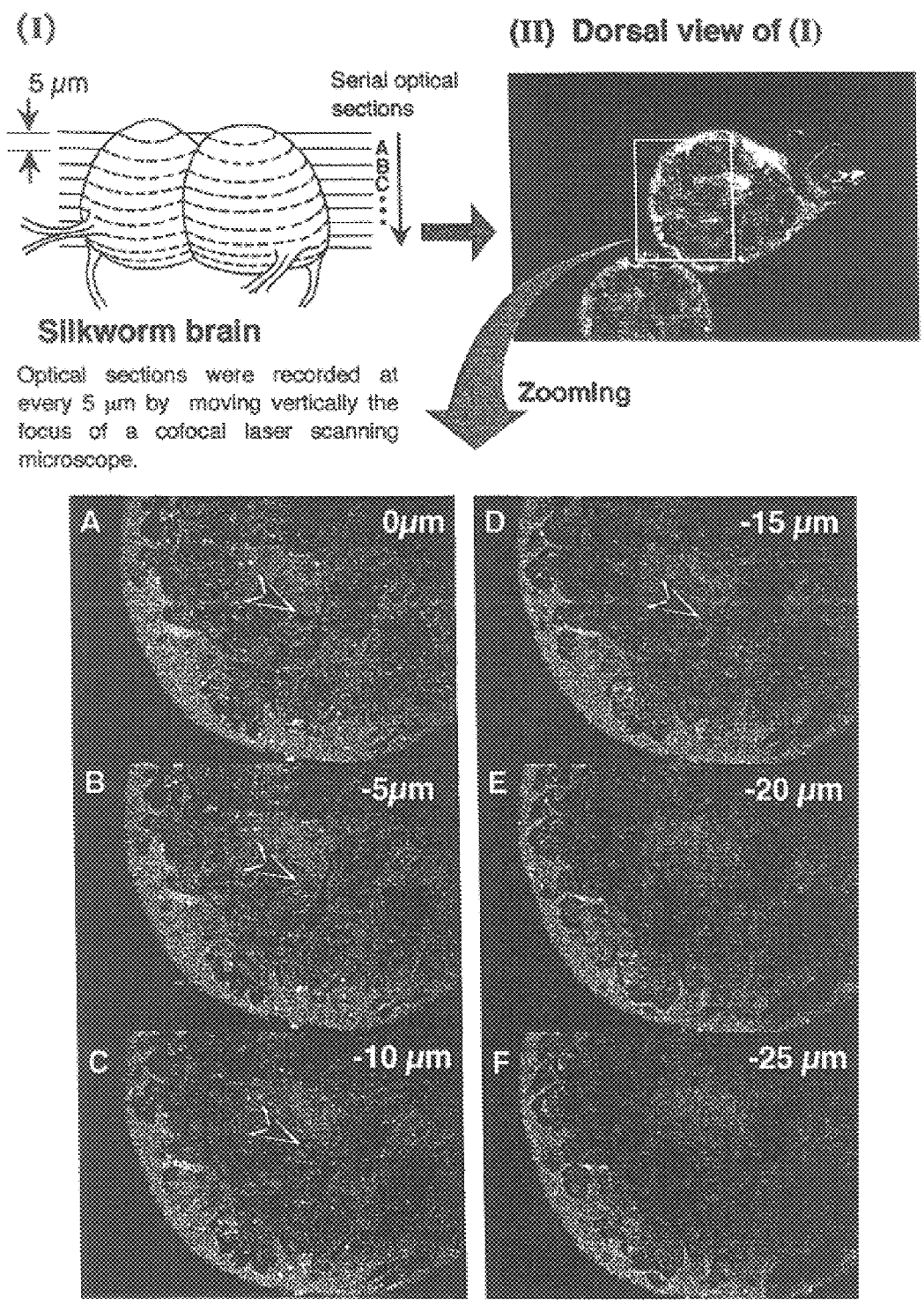
Fig. 5 Three dimensional imaging of 2-NBDG uptake in the silkworm brain.

FLUORESCENT IMAGING METHOD OF SACCHARIDE UPTAKE ACTIVITY OF LIVING TISSUE

BACKGROUND OF THE INVENTION

1. Field of the Invention

The present invention, in the field of biochemistry, particularly relates to a method for imaging the saccharide uptake activity of living cells which are in a state of maintaining biological activity and for obtaining information relating to changes in viability of living cells with external stimulations.

2. Description of the Prior Art

It is considered that the most universal indicator for representing the viability of living cells is an energy source uptake activity (uptake rate or uptake quantity). The typical example what of many of those cells can commonly take up as an energy source is glucose. However, no useful imaging methods for the glucose uptake activity has been developed until now.

Heretofore, as a method for imaging the glucose uptake activity in living bodies or tissues thereof, a 2-deoxyglucose (2-DG) method has been conducted. Namely, it is a method in that after a radioisotope labeled 2-deoxyglucose is incorporated instead of glucose, slices of living bodies or tissues thereof are observed by mean of autoradiography. However, this method does not allow, the bodies or tissues to be imaged as they are alive at real time, and requires complicated operations and is, furthermore, not sufficient in spatial resolution.

On the other hand, as techniques for imaging living bodies as they are intact, an X-ray CT, PET, MRI, etc. have already been developed. However, though these can image three-dimensionally, any of them have only a spatial resolution of about 0.1 mm, so that a resolution at a single cell level cannot be obtained. Alternatively, with an X-ray microscope and an atomic force microscope, a resolution superior to an optical microscope is obtained. However, they can image only appearances and shapes. Therefore, there still are many technical difficulties for obtaining images corresponding to the glucose uptake activity.

In order to image living bodies or tissues thereof having bioactivity (referred to as "living tissues, etc." hereinafter) as they maintain the bioactivity, namely, when they are alive, and to obtain, in combination with a microscope, spatial resolution at a single cell level, many fluorescent reagents have so far been developed. For example, mention may be made of (1) those having a fluorescence intensity or fluorescence wavelength which change with changes in the calcium ion concentrations or pH, (2) those having fluorescence intensity which change with changes in the surface potentials of cells, (3) those having a different permeability of the cell membrane between living cells and dead ones, (4) those which emitting fluorescence upon decomposition by a specific enzyme only in living cells, and (5) those combined with antibodies (fluorescence labeled antibody). If these fluorescent reagents are used, though information relating to living or dead cells, or information about responsiveness to exterior stimulation is obtainable, the information is not always said to be a general and universal indicator showing the viability of the cells of the living tissues, etc.

SUMMARY OF THE INVENTION

Therefore, the principal object of the present invention is to make it possible to image the saccharide uptake activity in living tissues, etc. by using a fluorescent saccharide reagent containing a fluorescent glucose derivative obtained by chemically modifying glucose, which is a common energy source for many cells such as the living tissues, etc.

Another object of the present invention is to effect observation and analysis of the saccharide metabolism in various living tissues, etc. by using a series of fluorescent saccharide compounds comprising fluorescent derivatives of glucose analogues, such as galactose, mannose, N-acetylglucosamine or the like, in combination with a fluorescent saccharide reagent comprising a fluorescent glucose compound.

Further, the ultimate object of the present invention is to establish a bioassay by obtaining in real time and assessing the changes in viability of the cells in the living tissues, etc. with exterior stimulations, namely, the changes in physiological function, and provide implements and apparatuses for this purpose.

The present invention to attain the above objects comprises mainly the establishment of a method for utilizing a fluorescent saccharide reagent in the bioassay of the living tissues, etc.

Firstly, the method for fluorescent-imaging the saccharide uptake activity in the living tissues, etc. according to the present invention is characterized in that an aqueous solution of a fluorescent saccharide compound which comprises at its specific position a saccharide molecule chemically combined with a fluorescent pigment molecule having a molecular weight of at most 300 is contacted with or administered to the living tissues, etc. and the above fluorescent saccharide compound is incorporated with the living tissues, etc.

Further, the imaging method of the viability of the living tissues, etc. according to the present invention comprises giving a chemical or physical exterior stimulation to the living tissues, etc. and obtaining information on changes in the viability of cells such as the living tissues, etc. with said stimulation, from a fluorescence imaging change of the saccharide uptake activity by the uptake of the above fluorescent saccharide compound.

The above exterior stimulation includes those which can give changes in the viability or physiological function of the living tissues, etc. such as chemical stimulation with medicaments, poisons, physiological active substances, and microorganisms such as virus and bacteria, and others, or physical stimulation with light, heat, pressure changes, sonic waves, electric fields, magnetic fields, electromagnetic fields, radioactivity, etc.

The above fluorescent saccharide reagent to be used in the fluorescence imaging method of the saccharide uptake activity or the viability of the living tissues, etc. includes an aqueous solution of a fluorescent saccharide compound having a specific position chemically bonded with a fluorescent pigment molecule having a molecular weight of at most 300. As the saccharide molecule, most preferred is glucose, and the above specific position is suited to be the C-2 position in glucose.

The typical example of such a fluorescent saccharide compound is 2-[N-(7-nitrobenz-2-oxa-1,3-diazol-4-yl) amino]-2-deoxy-D-glucose (referred to as "2-NBDG" hereinafter) as shown in the following chemical structural formula (1).

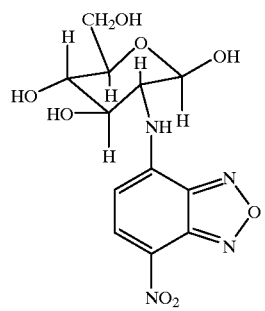

(1)

The above fluorescent saccharide reagent to be used in the imaging method of the saccharide uptake activity of the living tissues, etc. according to the present invention is preferred to contain the above fluorescent saccharide compound in a concentration of 10 μM to 10 mM.

Further, the implements and apparatuses for bioassay according to the present invention assess physiological functions of the above-mentioned exterior stimulation based on changes of the fluorescence imaging of the saccharide uptake activity of the living tissues, etc. and the result of the assessments is utilized.

The fluorescent saccharide compound which is a principal ingredient of the fluorescent saccharide reagent according to the present invention, comprises a fluorescent pigment molecule having a molecular weight of at most 300 combined with a specific position of the saccharide molecule. As such a saccharide, glucose is the most preferred, but not limited thereto. The present inventor has found that analogous saccharides such as galactose, mannose, N-acetylglucosamine or the like are also applicable.

Further, the above specific position is most preferred to be the C-2 position in glucose. For example, as shown in FIG. 1, D-glucosamine (GlcN) having an amino group substituted for hydroxyl group at the C-2 position of D-glucose is reacted with a fluorescent pigment molecule having a molecular weight not excessively greater than that of glucose (molecular weight: 180), particularly at most 300, for example, N-(7-nitrobenz-2-oxa-1,3-diazol-4-yl) aminochloride (molecular weight: 200, referred to as "NBD-Cl" hereinafter). Thus, the 2-NBDG (molecular weight: 342) shown in the aforementioned chemical structural formula (1), which is D-glucose having at its C-2 position an introduced NBD-Cl as a side chain, is a typical example of the compound to be used as a principal ingredient in the fluorescent saccharide reagent according to the present invention.

The reaction of GlcN with NBD-Cl readily proceeds, for example, in an aqueous solvent containing methanol, in the dark, preferably under stirring, at a temperature between about 20° C. and 40° C. and is completed in about 10 to 20 hours. If the above reaction temperature is too low, the reaction rate will be low, requiring a long reaction time, while if it is too high, a fear of a side reaction or decomposition of reaction products will be posed.

Thus, the 2-NBDG produced by a dehydrochlorination reaction between GlcN and NBD-Cl is separated and purified, for example, by means of a column chromatography, such as anion exchange column chromatography, gel filtration column chromatography and the like, to provide the aimed products with high purity. The obtained fluorescent saccharide compound is dissolved in a solvent such as water, physiological saline or the like, in an appropriate concentration, preferably 10 μM to 10 mM, to provide a fluorescent saccharide reagent. In particular, when it is intended to be injected into animal tissues, a higher concentration may be used.

The present inventor has produced fluorescent saccharide compounds corresponding to galactose, mannose, N-acetylglucosamine and others in the same manner and developed various fluorescent saccharide reagents.

The 2-NBDG having a molecular weight of 342, that is glucose with a molecular weight of 180 comprising, at its C-2 position, a side chain with a molecular weight of no more than about 300, is incorporated into living cells, as an equivalent compound to glucose. If the molecular weight of the side chain is greater than this, the living cells recognize it a substance different from glucose and exhibit different reactions, or deteriorate the saccharide uptake activity. Therefore, a side chain greater than 300 is not preferred.

Further, in the condition that either D-glucose or L-glucose and 2-NBDG coexisted with 2-NBDG, the 2-NBDG uptake rate was compared with respect of *Escherichia coli* and a yeast. It has been found that the 2-NBDG uptake is competitively inhibited only by D-glucose. Thereby, it is assumed that the 2-NBDG uptake is inherently conducted by a transport system for D-glucose to be incorporated into the cells.

The fluorescent saccharide reagent obtained as above is contacted with or administered by injection to an animal or plant individuals or tissues separated therefrom and soaked in an artificial medium as an objective. Then, the fluorescent saccharide compound is incorporated into the living tissues, etc. and the saccharide uptake activity can be imaged. The imaging can be obtained as two-dimensional image information, by direct continuous observation with a fluorescence microscope. Though its spatial resolution is determined by a microscope to be used for observation, a usual fluorescence microscope can provide a sufficient resolution at a single cell level.

Further, for example, with a confocal laser scanning fluorescent microscope, 3-dimensional stereoscopic image information with a resolution of about 1 μm can be continuously obtained in real time from the living tissues, etc. maintain biological activity. The obtained imaging can be extensively utilized in a series of bioassay for the viability of living cells as a universal and general indicator.

Heretofore, to study glucose transport in the brain, the distribution of 6-[N-(7-nitrobenz-2-oxa-1,3-diazol-4-yl) amino]-6-deoxyglucose (6-NBDG) in the mouse hippocampus was observed by a confocal laser scanning microscopy. Since this fluorescent glucose analogue is labeled with NBD at the 6-carbon position which is inherently phosphorylated, hexokinase widely existing in various organisms can not phosphorylate this glucose. Therefore, even if it is incorporated in cells, it will naturally come out of the cells immediately. In contrast, the 2-NBDG to be used in the present invention is rapidly phosphorylated after incorporation in the cells with the consequence that it will remain in the cells. The addition of phosphoric acid anionizes the neutral glucose and thus the 2-NBDG will hardly permeate cell membranes. Ultimately, in order to increase the sensitivity for imaging, it is important to accumulate the incorporated fluorescent glucose in the cells.

Such imaging with a high sensitivity has not been able to be obtained so far, and has a great feature in that the objective living tissues, etc. can be continuously observed in real time as they maintain a biological activity, which makes a series of bioassay possible. Namely, since this technique is applicable to all of the microorganism cells, cultured cells of animals and plants, living tissues, etc. and animal and plant individuals, a bioassay using any of them is made possible and the reagent is applicable in a very wide range.

Further, saccharide metabolism in various living tissues, etc. can be observed and analyzed by using the fluorescent glucose derivative in combination with other series of fluorescent saccharide compounds such as fluorescence derivatives of glucose analogues such as galactose, mannose, N-acetylglucosamine or the like.

BRIEF DESCRIPTION OF THE DRAWING

The above and other objects, features and advantages of the present invention will become more apparent from reading the following description of the preferred embodiments taken in connection with the accompanying drawings, wherein:

FIG. 1 is an illustrative chart showing the synthesis of a fluorescent saccharide compound which is a principal ingredient of a fluorescent saccharide reagent according to the present invention;

FIG. 2 is a graph comparing the saccharide uptake rates by *Escherichia coli*, when either D-glucose or L-glucose coexists with a fluorescent glucose compound;

FIG. 3 is an illustrative chart showing a method for imaging the 2-NBDG uptake activity by the brain of a silkworm when odor stimulation was given to the silkworm according to the method of the present invention;

FIG. 4 is a fluorescence microscopic photograph showing a two-dimensional imaging of the 2-NBDG uptake activity of the brain of a silkworm; A is the control group and B is the odor stimulation group shown in FIG. 3; and FIG. 5 is a confocal laser scanning fluorescent microscopic photograph showing a three-dimensional imaging of 2-NBDG uptake activity of the brain of the silkworm shown in FIG. 3.

DESCRIPTION OF THE PREFERRED EMBODIMENTS

The present invention will be explained specifically in more detail with reference to the attached drawing. However, these examples are not intended to limit the scope of the present invention.

SYNTHESIZING EXAMPLE

The fluorescent glucose compound to be used as the fluorescent saccharide reagent in the present invention was synthesized as shown in FIG. 1. Namely, in order to introduce a fluorescent pigment into the C-2 position of glucose, GlcN and NBD-Cl were reacted in an aqueous alcohol solution (pH:7) at 25° C. in the dark, while stirring. The reaction product obtained after 15 hours was separated and purified by column chromatography (DEAE Sephadex A-50). The purity of the putative fluorescent glucose compound was confirmed with high performance liquid chromatography (HPLC) and then the objective product, 2-NBDG, was confirmed with $^1$NMR and mass spectrometry.

With respect to the analogous saccharides, such as galactose, mannose, N-acetylglucosamine, or the like, the corresponding fluorescent saccharide compounds were synthesized in the same manner as above.

Example 1

It was confirmed with cells of coliform bacillus, *E. coli*, and a yeast that the 2-NBDG (molecular weight: 342), which was a glucose derivative (molecular weight: 180) having at its C-2 position a side chain of molecular weight of at most 300, was incorporated equivalently to glucose. The graph shown in FIG. 2 is a result of the *coliform bacillus*. Namely, *coliform bacilli* (*E. coli*) were soaked in fluorescent saccharide reagents in which 10 μM of the 2-NBDG coexisted with various concentrations of 0~10,000 μM of D-glucose or L-glucose, and 2-NBDG uptake rates were investigated. As is apparent from the graph, the 2-NBDG uptake initial rate was substantially constant, irrespective of the concentration of L-glucose. However, when D-glucose coexisted, the uptake initial rate decreased rapidly with an increase in the D-glucose concentration, to substantially be near 0 when about a 10 fold concentration of the D-glucose coexisted. This suggested that the 2-NBDG uptake was competitively inhibited only by D-glucose, and the 2-NBDG uptake had been conducted inherently by a transport system for the incorporation of D-glucose into cells. With respect to the yeasts, the same result was obtained.

Example 2

The test for incorporating the 2-NBDG into living tissues taken out of animal or plant individuals can be performed in the same manner as with the microorganisms, such as *E. coli* or a yeast, in the above Example 1. In the case of the imaging of the glucose uptake activity of animal or plant individuals, setting up conditions were more difficult, and conducted as follows:

With respect to the brain of a silkworm, as shown in the illustrative chart of FIG. 3, 5th-instar silkworms were anesthetized by steeping in water for 30 minutes, and then 30 μl of 10 mM 2-NBDG were injected into the head of the silkworms. The silkworms were divided into two groups: "odor stimulation group" in which the silkworm container received mulberry green leaves, and "control group" in which the silkworm container received no leaf. The brains of the silkworms of the two groups were extracted at every constant time interval, and observed with a confocal laser scanning fluorescence microscope. The results are shown in the microscopic photograph of FIG. 4. As compared with the control group shown in A of FIG. 4, the odor stimulation group shown in B increased its fluorescence with the elapse of time, and it was found that the 2-NBDG uptake activity was extremely high. Namely, the silkworms recognized the odor stimulation of mulberry green leaves, with the consequence that they moved towards the direction of the odor stimulation and at the same time the acquisition of energy source in the brain, i.e. the saccharide uptake activity, was expected to be increased. The imaging as expected was obtained. As shown above, by using a fluorescence saccharide reagent containing the 2-NBDG, the imaging of the saccharide uptake activity of living tissues was made possible.

Example 3

The above example 2 showed imaging which was obtained as two-dimensional image information by direct continuous observation. However, if a confocal laser scanning fluorescence microscope is used, three-dimensional stereoscopic image information is also obtainable. The photomicrograph of FIG. 5 shows a 2-NBDG uptake activity after an hour of the brain of the silkworm shown in FIG. 4. In FIG. 5, as shown in (I) with dotted lines, in the brain tissues of the silkworm, the focal point of the confocal laser scanning fluorescence microscope to observe the brain tissues is slipped down successively by 5 μm, whereby optical slices A, B, C, D, E and F are obtained. The images taken from the above within the frame (II) were shown in photomicrographs A, B, C, D, E and F, respectively, in FIG. 5. By the thus obtained sectional imaging, stereoscopic image information is continuously obtained with a spatial resolution of about 1 μm as the living tissues, etc. maintain physiological activity. Therefore, the imaging of the present invention provides universal and general information about the viability of cells.

The present invention has the above-described structures, and with respect to animal or vegetable individuals or tissues separated therefrom and steeped in an artificial medium, information relating to changes of cell viability, when various chemical or physical stimulations are given, is obtainable from the changes in imaging of the saccharide uptake activity. Particularly, it is a remarkable feature that a continuous observation is possible over their cross-sections in real time as the objective living tissues, etc. are alive. This invention can be widely utilized in the discovery of medicaments, poisons and various physiologically active substances, assessment of activities thereof, analysis of functioning, etc.

Utilizing the excellent utilities of the present invention, various instruments, apparatuses and materials for bioassay, such as kits for imaging saccharide uptake activity and the like can be produced. Namely, the present invention is very important as a technique for assisting in the studies of life science and a basic technique for industry.

What is claimed is:

1. A method of detecting the saccharide uptake activity of living tissue containing living bodies having biological activity comprising the steps of: forming an aqueous solution of a fluorescent saccharide compound comprising a saccharide molecule chemically combined at a specific position thereof with a fluorescent pigment molecule having a molecular weight no greater than 300; contacting said tissue with said aqueous solution of the fluorescent saccharide compound such that said fluorescent saccharide compound is incorporated therein; and analyzing the tissue having the fluorescent saccharide compound incorporated therein with a fluorescence detection device.

2. The method of claim 1, wherein said saccharide is selected from the group consisting of galactose, mannose and N-acetylglucosamine.

3. The method of claim 1, additionally comprising the step of chemically or physically stimulating the exterior of the tissue prior to analyzing the tissue with the fluorescence detection device.

4. The method according to claim 1, wherein said saccharide molecule is glucose, and said specific position is the C-2 position in the glucose.

5. The method according to claim 1, wherein said fluorescent saccharide compound is 2-[N-(7-nitrobenz-2-oxa-1,3-diazol-4-yl)amino]-2-deoxy-D-glucose.

6. The method according to claim 1, wherein said fluorescent saccharide compound is contained at a concentration of 10 μM to 10 mM in the aqueous solution.

7. The method according to claim 3, wherein said exterior stimulation is any one of chemical stimulation with medicaments, poisons, microorganisms, and physical stimulation with light, heat, pressure changes, sonic waves, electric fields, magnetic fields, electromagnetic fields and radioactivity.

* * * * *